(12) United States Patent
Engstrand et al.

(10) Patent No.: US 7,867,784 B2
(45) Date of Patent: Jan. 11, 2011

(54) CHROMATOGRAPHY LIGAND

(75) Inventors: Carina Engstrand, Uppsala (SE); Annika Forss, Uppsala (SE); Gunnar Glad, Uppsala (SE); Bo-Lennart Johansson, Uppsala (SE); Hans J. Johansson, Uppsala (SE); Jean-Luc Maloisel, Uppsala (SE)

(73) Assignee: GE Healthcare Bio-Science AB, Uppsala (SE)

( * ) Notice: Subject to any disclaimer, the term of this patent is extended or adjusted under 35 U.S.C. 154(b) by 571 days.

(21) Appl. No.: 11/577,208

(22) PCT Filed: Oct. 21, 2005

(86) PCT No.: PCT/SE2005/001592

§ 371 (c)(1),
(2), (4) Date: Apr. 13, 2007

(87) PCT Pub. No.: WO2006/043896

PCT Pub. Date: Apr. 27, 2006

(65) Prior Publication Data

US 2007/0244307 A1   Oct. 18, 2007

(30) Foreign Application Priority Data

Oct. 21, 2004 (SE) .................................. 0402558
Nov. 26, 2004 (SE) .................................. 0402910

(51) Int. Cl.
*G01N 33/544* (2006.01)
*G01N 33/548* (2006.01)
*G01N 33/551* (2006.01)
*C12M 1/34* (2006.01)
*C07C 211/44* (2006.01)

(52) U.S. Cl. ................. 436/528; 436/524; 436/529; 436/530; 435/287.2; 564/305

(58) Field of Classification Search .................. None
See application file for complete search history.

(56) References Cited

U.S. PATENT DOCUMENTS 2,405,555 A   8/1946   Bergel et al.

(Continued)

FOREIGN PATENT DOCUMENTS

WO   WO84/00773   3/1984

(Continued)

OTHER PUBLICATIONS

Graves et al. Interaction of N-substituted ethanolamine analogs with ethanolamine ammonia-lyase, an adensylcobalamin-requiring enzyme. J. Biol. Chem. 1982, Vo. 257, No. 8, pp. 4102-4105.*

(Continued)

*Primary Examiner*—Shafiqul Haq
(74) *Attorney, Agent, or Firm*—Yonggang Ji

(57) ABSTRACT

The present invention relates to a chromatography ligand defined by the following formula (I) $R_1$—$R_2$—$N(R_3)$—$R_4$—$R_5$ wherein $R_1$ is a substituted or non-substituted phenyl group; $R_2$ is a hydrocarbon chain comprising 0-4 carbon atoms; $R_3$ is a hydrocarbon chain comprising 1-3 carbon atoms; $R_4$ is a hydrocarbon chain comprising 1-5 carbon atoms; and $R_5$ is OH or H. The invention also comprises a separation matrix, comprising the described ligands coupled to a porous support, such as particles or a membrane. The ligand and matrix according to the invention is useful for purification of biomolecules or organic compounds, such as proteins, polypeptides, DNA etc. An advantageous use according to the invention is the purification of antibodies.

1 Claim, 7 Drawing Sheets

U.S. PATENT DOCUMENTS

| | | | |
|---|---|---|---|
| 4,983,722 | A | 1/1991 | Bloom et al. |
| 5,151,350 | A | 9/1992 | Colbert et al. |
| 5,322,859 | A | 6/1994 | Schoenwald et al. |
| 5,429,746 | A | 7/1995 | Shadle et al. |
| 5,908,960 | A | 6/1999 | Newlander |
| 5,945,520 | A | 8/1999 | Burton et al. |
| 6,428,707 | B1 | 8/2002 | Berg et al. |
| 6,498,236 | B1 | 12/2002 | Lihme et al. |
| 6,602,990 | B1 | 8/2003 | Berg |
| 6,702,943 | B1 * | 3/2004 | Johansson et al. ............ 210/635 |
| 6,794,519 | B2 | 9/2004 | Kano et al. |

FOREIGN PATENT DOCUMENTS

| | | |
|---|---|---|
| WO | WO01/38227 | 5/2001 |
| WO | WO01/38228 | 5/2001 |
| WO | WO02/053252 | 7/2002 |
| WO | WO03/041859 | 5/2003 |
| WO | WO2004/076485 | 9/2004 |
| WO | WO2006/033634 | 3/2006 |
| WO | WO2006/043895 | 4/2006 |

OTHER PUBLICATIONS

Crowther, J., et al., "High-Performance liquid chromatographic separation of oligonucleotides and other nucleic acid constituents on multifunctional stationary phases" Journal of Chromatography, Elsevier Science Publishers B.V. Amsterdam, NL, vol. 282, Jan. 1, 1983, p. 619-628.

Buck, J., et al., "Preparation of secondary amines" J.A.C.S., vol. 63, No. 7, 1941, p. 1964-1966.

Johansson, B-L, et al., "Preparation and characterization of prototypes for multi-modal separation media aimed for capture of negatively charged biomolecules at high salt conditions" Journal of Chromatography, Elsevier Science Publishers B.V. Amsterdam, NL, vol. 1016, No. 1, Oct. 17, 2003, p. 21-33.

Arshady, R. (Sep. 1988). "Styrene Based Polymer Supports Developed by Suspension Polymerization". La Chimica E L'Industria, 70(9), 70-75.

Blank, G. S., Zapata, G., Fahrner, R., Milton, M., Yedinak, C., Knudsen, H. & Schmelzer, C. (2001). "Expanded bed adsorption in the purification fo monoclonal antibodies: a comparison of process alternatives". Bioseparation, 10, 65-71.

Burton, S. C. & Harding, D. R. K. (2001). "Salt-independent adsorption chromatography: new broad-spectrum affinity methods for protein capture". Journal of Biochemical and Biophysical Methods, 49, 275-287.

Habtermariam, A., Watchman, B., Potter, B. S., Palmer, R., Parsons, S., Parkin, A. & Sadler, P. J. (2001). "Control of aminophosphine chelate ring-opening in Pt(II) and Pd(II) complexes: potential dual-mode anticancer agents". The Royal Society of Chemistry, 1306-1318.

Hansen, M. B., Lihme, A., Spitali, M. & King, D. (1999). "Capture of human Fab fragments by expanded bed adsorption with a mixed mode adsorbent". Bioseparation, 8, 189-193.

Hermanson, G. T., Mallia, A. K., & Smith, P. K. (1992). "Immobilized Affinity Ligand Techniques" (p. 118). San Diego, CA: Academic Press.

Hjerten, S. (1964). "The Preparation of Agarose Spheres for Chromatography of Molecules and Particles". Biochimica et Biophysica Acta, 79, 393-398.

Johansson, B., Belew, M., Eriksson, S., Glad, G., Lind, O., Maloisel, J. & Norrman, N. (2003). "Preparation and characterization of prototypes for multi-modal separation aimed for capture of positively charged biomolecules at high salt conditions". Journal of Chromatography A, 1016, 35-49.

Karger, B. L., Snyder, L. R. & Horvath, C. (1973). "An Introduction to Separation Science" (p. 42). New York, NY: John Wiley & Sons.

Kaster, M. (Eds.). (2000). "Protein liquid chromatography" (vol. 61, pp. 81-88). Amsterdam and New York: Elsevier.

Knudsen, H. L., Fahrner, R. L., Xu, Y., Norling, L. A. & Blank, G. S. (2001). "Membrane ion-exchange chromatography for process-scale antibody purification". Journal of Chromatography A, 907, 145-154.

Nau, D. R. (Nov. 29, 2004). "Chromatographic Method For The Purification of Therapeutic-Grade Monoclonal Antibodies" (Online), retrieved May 3, 2005 from http://www.jtbaker.com/techlib/documents/8013.html.

* cited by examiner

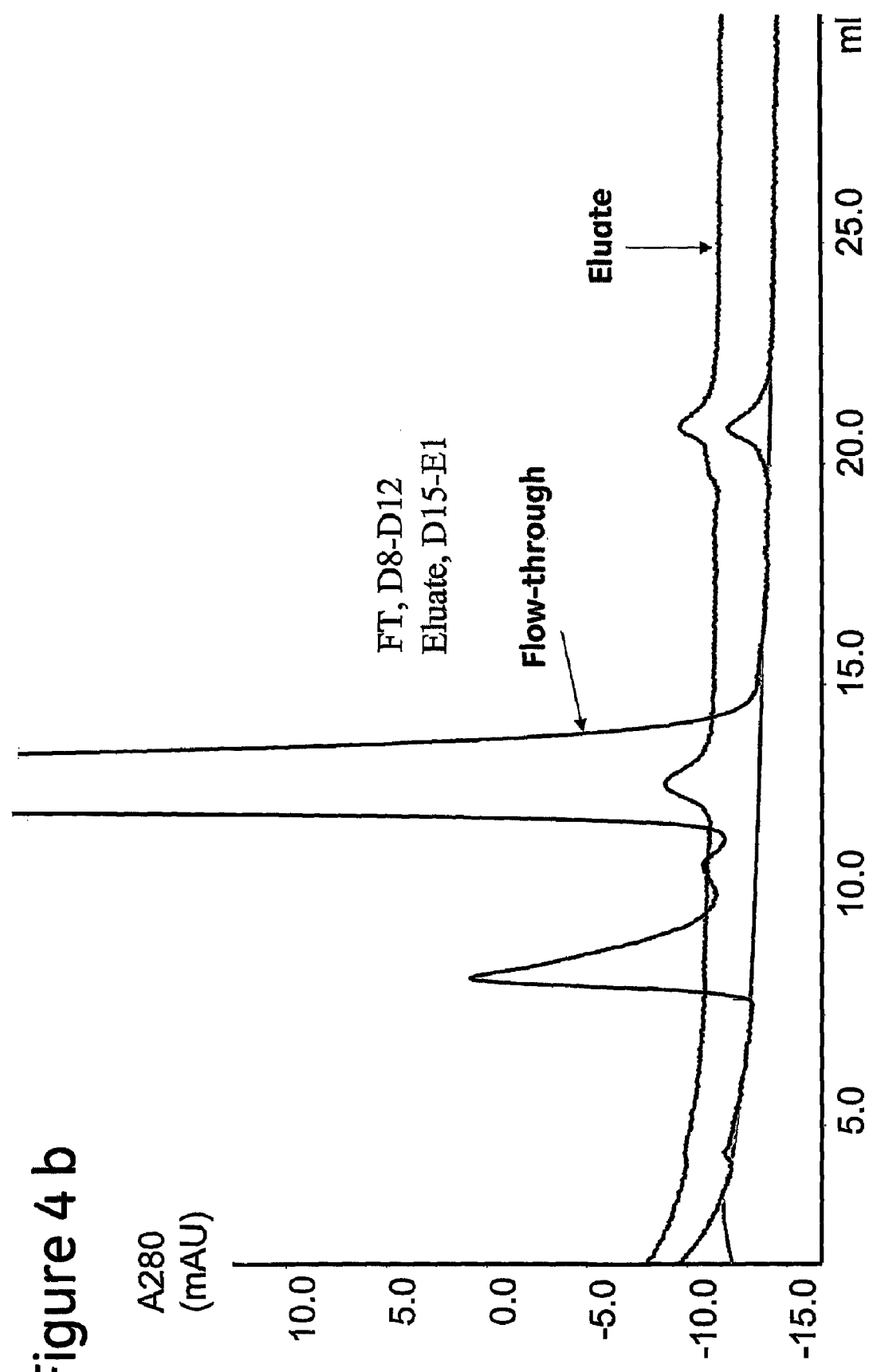

CHROMATOGRAPHY LIGAND

TECHNICAL FIELD

The present invention relates to novel chromatography ligands, which are useful for the purification of biomolecules such as proteins. The present ligands are useful e.g. for the purification of antibodies, preferably immobilised to a porous support such as particles or a membrane. Consequently, the invention also encompasses a chromatography matrix comprising the novel ligands, a method for the preparation thereof and a kit for the purification of antibodies.

BACKGROUND

The immune system is composed of many interdependent cell types that collectively protect the body from bacterial, parasitic, fungal, viral infections and from the growth of tumour cells. The guards of the immune system are macrophages that continually roam the bloodstream of their host. When challenged by infection or immunisation, macrophages respond by engulfing invaders marked with foreign molecules known as antigens. This event, mediated by helper T cells, sets forth a complicated chain of responses that result in the stimulation of B-cells. These B-cells, in turn, produce proteins called antibodies, which bind to the foreign invader. The binding event between antibody and antigen marks the foreign invader for destruction via phagocytosis or activation of the complement system. A number of different classes of antibodies, also known as immunoglobulins, exist, such as IgA, IgD, IgE, IgG, and IgM. They differ not only in their physiological roles but also in their structures. From a structural point of view, IgG antibodies have been extensively studied, perhaps because of the dominant role they play in a mature immune response. Polyclonal antibodies are produced according to standard methods by immunisation of an animal with the appropriate antigen. In response, the animal will produce antibodies which are polyclonal. However, for many purposes, it is desired to have a single clone of a certain antibody, known as monoclonal antibodies. Monoclonal antibodies (MAbs) are produced by hybrid or fused cells comprised of a fusion between a normal B-cell, which produces only a single antibody, to an abnormal myeloma tumour cell. The resulting hybrid, known as a hybridoma, is these days used in standard methods for the production of antibodies.

The biological activity that the immunoglobulins possess is today exploited in a range of different applications in the human and veterinary diagnostic, health care and therapeutic sector. In fact, in the last few years, monoclonal antibodies and recombinant antibody constructs have become the largest class of proteins currently investigated in clinical trials and receiving FDA approval as therapeutics and diagnostics. Complementary to expression systems and production strategies, efficient purification protocols are required to obtain highly pure antibodies in a simple and cost-efficient manner.

Traditional methods for isolation of immunoglobulins are based on selective reversible precipitation of the protein fraction comprising the immunoglobulins while leaving other groups of proteins in solution. Typical precipitation agents are ethanol, polyethylene glycol, lyotropic salts such as ammonium sulphate and potassium phosphate, and caprylic acid. Typically, these precipitation methods are giving very impure products while at the same time being time consuming and laborious. Furthermore, the addition of the precipitating agent to the raw material makes it difficult to use the supernatant for other purposes and creates a disposal problem, which is particularly relevant when speaking of large-scale purification of immunoglobulins.

An alternative method for isolation of immunoglobulins is chromatography, which embraces a family of closely related separation methods. The feature distinguishing chromatography from most other physical and chemical methods of separation is that two mutually immiscible phases are brought into contact wherein one phase is stationary and the other mobile. The sample mixture, introduced into the mobile phase, undergoes a series of interactions with the stationary and mobile phases as it is being carried through the system by the mobile phase. Interactions exploit differences in the physical or chemical properties of the components in the sample. These differences govern the rate of migration of the individual components under the influence of a mobile phase moving through a column containing the stationary phase. Separated components emerge in the order of increasing interaction with the stationary phase. The least retarded component elutes first, the most strongly retained material elutes last. Separation is obtained when one component is retarded sufficiently to prevent overlap with the zone of an adjacent solute as sample components elute from the column. Efforts are continuously being made to design the optimal stationary phase for each specific separation purpose. Such a stationary phase is commonly comprised of a support or base matrix to which a ligand comprising functional i.e. binding groups has been attached. Reference is commonly made to each kind of chromatography based on the principle of interaction it utilises, such as affinity chromatography, hydrophobic interaction chromatography and ion-exchange chromatography.

Affinity chromatography is based on specific interactions between a target biomolecule and a biospecific ligand according to a principle of lock-key recognition. Thus, the target and ligand will constitute an affinity pair, such as antigen/antibody, enzyme/receptor etc. Protein-based affinity ligands are well known, such as Protein A and Protein G affinity chromatography which are both widespread methods for isolation and purification of antibodies. It is well known that Protein A chromatography provides an outstanding specificity, particularly towards monoclonal antibodies, and consequently high purities are obtainable. Used in combination with ion exchange, hydrophobic interaction, hydroxyapatite and/or gel filtration steps, Protein A-based methods have become the antibody purification method of choice for many biopharmaceutical companies, see e.g. WO 8400773 and U.S. Pat. No. 5,151,350. However, due to the peptide bonds of the proteins, protein A matrices present a certain degree of alkaline sensitivity. In addition, when Protein A matrices are used to purify antibodies from cell culture media, proteases originating from the cells may cause leakage of Protein A, or peptide fragments thereof.

Ion exchange chromatography is frequently used in protocols for the isolation of immunoglobulins. In anion exchange chromatography, negatively charged amino acid side chains of the immunoglobulin will interact with positively charged ligands of a chromatography matrix. In cation exchange chromatography on the other hand, positively charged amino acid side chains of the immunoglobulin will interact with negatively charged ligands of a chromatography matrix.

Hydrophobic interaction chromatography (HIC) is another method described and used in protocols for the isolation of immunoglobulins. If a highly pure immunoglobulin product is the object, it is commonly recommended to combine HIC with one or more further steps. In HIC, in order to make the immunoglobulin bind efficiently to the HIC matrix, addition of lyotropic salts to the mobile phase is required. The bound immunoglobulin is subsequently released from the matrix by lowering the concentration of lyotropic salt. Thus, a disadvantage of this procedure is the necessity to add lyotropic salt to the raw material, as this may cause problems and a consequently increased cost to the large-scale user. For example, for raw materials such as whey, plasma, and egg yolk, the addition of lyotropic salts to the raw materials would in many instances be prohibitive in large-scale applications, as the salt could prevent any economically feasible use of the immunoglobulin depleted raw material. An additional problem in large-scale applications would be the disposal of several thousand litres of waste.

U.S. Pat. No. 5,945,520 (Burton et al) discloses mixed mode chromatographic resins which exhibit a hydrophobic character at the pH of binding and a hydrophilic and/or electrostatic character at the pH of desorption. The resin is specifically designed to bind the target compound from an aqueous solution at both a low and high ionic strength. This is achieved by selected ionisable ligands comprising a spacer arm and at least one ionisable functionality, wherein the density of the ionisable ligands on the solid support matrix is greater than the smaller of either about 150 μmol/mL resin or 1 mmol/gram dry weight of resin. In addition, the hydrophobic character of the resin comprising said ionisable ligands is sufficient to bind at least 50% of the target compound in an aqueous medium at high and low ionic strength at a first pH. Illustrative examples of the ionisable functionality are 4-(aminomethyl)pyridine, 3-(aminomethyl)pyridine, 2-(aminomethyl)pyridine, 1-(3-aminopropyl)-imidazole, 2-(aminomethyl)-benzimidazole, 4-(3-aminopropyl)morpholine.

Further, WO 01/38228 (Belew et al.) relates to a method for anion-exchange adsorption wherein thioether anion-exchangers are used to remove a negatively charged substance from a liquid by binding thereof. Each ligand comprises a positively charged nitrogen and a thioether linkage at a distance of 1-7 atoms from said charged nitrogen. The desired substances, such as cells, parts of cells and substances comprising peptide structures are adsorbed at salt concentrations in the region of 0.25M NaCl.

Finally, U.S. Pat. No. 6,702,943 (Johansson et al) discloses a method for removal of a target substance from a liquid by adsorption thereof to a matrix carrying a plurality of ligands comprising anion-exchanging groups and a hydrophobic structure. More specifically, the ligands contain an aromatic ring in the proximity of the positively charged anion-exchanging groups. The desired substances are stated to be cells, parts of cells and substances comprising peptide structures. The ligands disclosed are denoted "high salt ligands" due to their capability of adsorbing target substances at high concentrations of salt such as 0.25M NaCl.

However, to optimise a process related to the purification of a specific target molecule, unique operating conditions will be required, and the best separation matrix will vary from case to case. For example, in the biotech industry, specific processes need to be designed for the purification of peptides and proteins; nucleic acids; virus etc. Further, in the purification of antibodies, the type of antibody will decisive for the choice of separation matrix. Thus, there is still a need in this field of alternative separation matrices to provide a broad spectrum of choices for the purification of the many new products that are constantly developed.

BRIEF DESCRIPTION OF THE INVENTION

One aspect of the present invention is to provide a novel ligand which is useful in the separation of antibodies from other components of a liquid.

A specific aspect of the invention is to provide such a ligand, which is capable of adsorbing contaminating proteins but not the target antibody.

Further aspects and advantages of the invention will appear from the detailed description that follows.

DEFINITIONS

Figure 1:
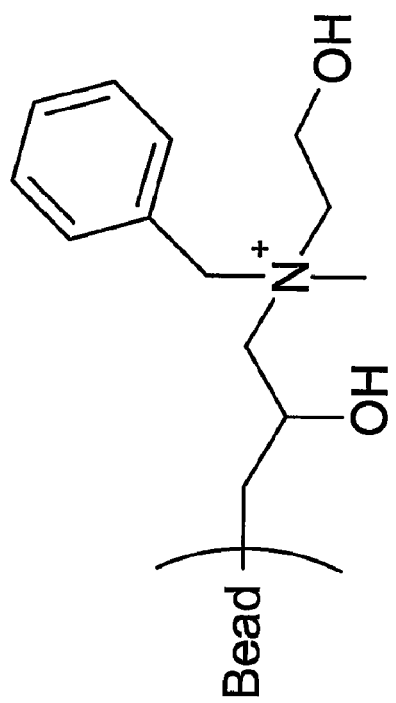
FIG. 1 is an illustrative chromatography ligand according to the invention, namely N-benzyl-N-methyl ethanolamine coupled to a support via its amine.
Figure 1:
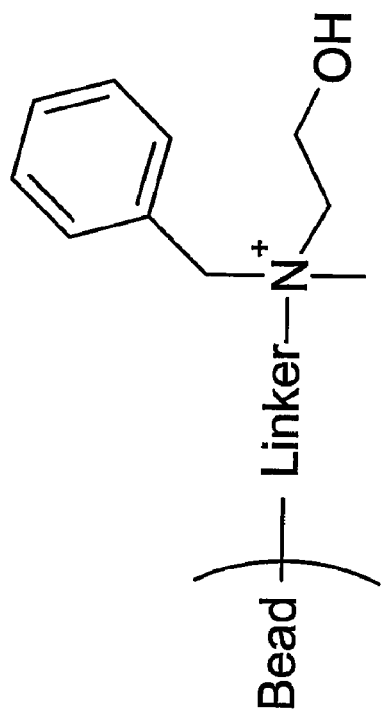

The terms "antibody" and "immunoglobulin" are used interchangeably in the present specification.

The term "separation matrix" is used herein to denote a material comprised of a support to which one or more ligands comprising functional groups have been coupled. The term "resin" is sometimes used for a separation matrix in this field.

The term "multi-modal" separation matrix refers to a matrix capable of providing at least two different, but co-operative, sites which interact with the compound to be bound. For example, one of these sites may give an attractive type of charge-charge interaction between the ligand and the substance of interest. The other site may give electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. "Multi-modal" separation matrices are also known as "mixed mode" separation matrices.

The term "surface" means herein all external surfaces, and includes in the case of a porous support outer surfaces as well as pore surfaces.

The term "eluent" is used in its conventional meaning in this field, i.e. a buffer of suitable pH and/or ionic strength to release one or more compounds from a separation matrix.

The term "capture step" refers in the context of liquid chromatography to the initial step of a separation procedure. Most commonly, a capture step includes clarification, concentration, stabilisation and a significant purification from soluble impurities. After the capture step, an intermediate purification may follow, which further reduces remaining amounts of impurities such as host cell proteins, DNA, viruses, endotoxins, nutrients, components of a cell culture medium, such as antifoam agents and antibiotics, and product-related impurities, such as aggregates, misfolded species and aggregates. The term "disposable" means herein in the context of chromatography columns and other separation matrices a matrix which is intended for single use, or a limited number of uses. Disposable products are advantageously used to remove contaminants which are harmful even in very small amounts, in which case it is convenient to adsorb said contaminant to the matrix and then discard the matrix.

Another situation when disposable products are desired is for sterile processing, in which case the matrix is sterile or at least aseptic.

The term "polishing step" refers in the context of liquid chromatography to a final purification step, wherein trace impurities are removed to leave an active, safe product. Impurities removed during the polishing step are often conformers of the target molecule or suspected leakage products.

The term an "Fc-binding protein" means a protein capable of binding to the crystallisable part (Fc) of an antibody and includes e.g. Protein A and Protein G, or any fragment or fusion protein thereof that has maintained said binding property.

DETAILED DESCRIPTION OF THE INVENTION

In a first aspect, the present invention is a chromatography ligand comprising an aromatic ethanolamine. The ligand according to the invention is especially useful in the purification of antibodies, as will be discussed in more detail below.

In a first embodiment, the present ligand is defined by the following formula

wherein
  $R_1$ is a substituted or non-substituted aromatic ring system, such as a phenyl group;
  $R_2$ is a hydrocarbon chain comprising 0-4 carbon atoms;
  $R_3$ is a hydrocarbon chain comprising 1-3 carbon atoms;
  $R_4$ is a hydrocarbon chain comprising 1-5 carbon atoms; and
  $R_5$ is OH or H.

As appears from the above, the group $R_1$ is connected to the amine via a carbon chain $R_2$ that may comprise no carbon atoms, i.e. constitute a bond between $R_1$ and the amine; or 1-4 carbon atoms, such as 2-3 carbon atoms, which are optionally substituted. The carbon chain $R_4$ connecting the amine with the $R_5$ may comprise 1-5 carbon atoms, such as 2-4 carbon atoms, which are optionally substituted. $R_3$ of the amine may comprise 1-3 carbon atoms, such as 2 carbon atoms, which are optionally substituted.

The aromatic ring system $R_1$ may comprise one or more substituted or non-substituted phenyl groups, provided the substitution(s) do not impair the binding properties of the ligand to any substantial extent. Thus, $R_1$ may comprise one or more aromatic rings, for instance a phenylene, a biphenylene or a naphthylene structure and other aromatic ring systems. Aromatic rings may be heterocyclic, i.e. contain one or more nitrogen, oxygen or sulphur atoms, for instance a pyridine, pyrimidine, pyrrole, imidazole, thiophene, or pyran. Illustrative substituted $R_1$ groups are selected from the group consisting of hydoxyphenyl (2-, 3- and 4-); 2-benzimadozolyl; methylthioxyphenyl (2-, 3- and 4-); 3-indolyl; 2-hydroxy-5-nitrophenyl; aminophenyl (2-, 3- and 4-); 4-(2-aminoethyl) phenyl; 3,4-dihydroxyphenyl; 4-nitrophenyl; 3-trifluoromethylphenyl; 4-imidazolyl; 4-aminopyridine; 6-aminopyrimidyl; 2-thienyl; 2,4,5-triaminophenyl; 4-aminotriazinyl; and 4-sulphoneamidophenyl.

In an advantageous embodiment, $R_1$ is non-substituted phenyl. In an alternative embodiment, $R_1$ is phenyl substituted with one or more OH groups.

Further, one or more of $R_1$, $R_2$, $R_3$, and $R_4$ may be substituted with any suitable substituent, as long as the binding properties of the ligand are not impaired to any substantial extent. For example, if a more hydrophilic ligand is desired, it may comprise one or more hydrophilic groups, such as OH groups. Alternatively, substitution may increase the hydrophobicity of the ligand, in which case the ligand may comprise one or more hydrophobic groups, such as alkyl and/or fluorine. Finally, substitution may be used to introduce one or more additional functionalities, such as charged entities, too increase the multi-modal character of the ligand. Further, the carbon chains $R_2$ and $R_3$ may be linear or branched, as long as the branches do not impair the binding properties of the ligand to any substantial extent.

In a specific embodiment of the present ligand, $R_2$ is —$CH_2$—. In another embodiment, $R_3$ is —$CH_3$. In a further embodiment, $R_4$ is —$CH_2$—$CH_2$—$CH_2$— or —$CH_2$—$CH_2$—. In yet another embodiment, $R_1$ is non-substituted phenyl.

Thus, in an advantageous embodiment, the ligand according to the invention comprises N-benzyl-N-methyl ethanol amine (BMEA). In an alternative embodiment, the ligand is N,N-dimethylbenzylamine.

The ligand according to the invention is easily synthesised by the skilled person in this field using standard methods in organic chemistry.

A further aspect of the invention is a method of preparing a separation matrix, which method comprises immobilising a plurality of ligands as described above to a support. In order to provide a matrix suitable for single use especially in the medical or diagnostic field, the separation matrix prepared according to the invention is also sterilised in a subsequent step. Thus, in one embodiment, the method comprises preparing a matrix as described above; providing the matrix so prepared in a column; and sterilizing the matrix so prepared. Sterilization is easily carried out under suitable conditions by the skilled person in this field, such as be heat treatment; radiation; or any other conventionally used method.

As appears from the formula above, in its non-immobilised state, the ligand according to the invention comprises a tertiary amine which will constitute a suitable handle for coupling the thereof to a support, thus creating a coupled ligand which comprises a quaternary amine and a phenyl group. Consequently, as immobilized, the ligand according to the invention is considered to be a multi-modal anion exchange ligand, since in addition to the positively charged quaternary amine group it also comprises the aromatic ring structure which is hydrophobic. Methods for immobilisation of ligands to porous or non-porous surfaces are well known in this field; see e.g. Immobilized Affinity Ligand Techniques, Hermanson et al, Greg T. Hermanson, A. Krishna Mallia and Paul K. Smith, Academic Press, INC, 1992. In one embodiment, the ligands density at the surface of the support is in a range close to what is commonly used for conventional ion-exchange matrices.

In an advantageous embodiment, the coupling of the ligand to the support is provided by introducing a linker between the support and linker. The coupling may be carried out following any conventional covalent coupling methodology such as by use of epichlorohydrin; epibromohydrin; allyl-glycidylether; bis-epoxides such as butanedioldiglycidylether; halogen-substituted aliphatic substances such as di-chloro-propanol; and divinyl sulfone. These methods are all well known in the field and easily carried out by the skilled person.

In a specific embodiment, the ligand according to the invention is coupled to the support via a longer linker molecule, also known as extender. Extenders are well known in this field, and commonly used to increase sterically the distance between ligand and support. Extenders are sometimes denoted tentacles or flexible arms, for a more detailed description of possible chemical structures, see e.g. U.S. Pat. No. 6,428,707, which is hereby included herein via reference.

In brief, the extender may be in the form of a polymer such as a homo- or a copolymer. Hydrophilic polymeric extenders may be of synthetic origin, i.e. with a synthetic skeleton, or of biological origin, i.e. a biopolymer with a naturally occurring skeleton. Typical synthetic polymers are polyvinyl alcohols, polyacryl- and polymethacrylamides, polyvinyl ethers etc. Typical biopolymers are polysaccharides, such as starch, cellulose, dextran, agarose.

The support may be made from an organic or inorganic material, and may be porous or non-porous. In one embodiment, the support is prepared from a native polymer, such as cross-linked carbohydrate material, e.g. agarose, agar, cellulose, dextran, chitosan, konjac, carrageenan, gellan, alginate, pectin, starch, etc. The native polymer supports are easily prepared and optionally cross-linked according to standard methods, such as inverse suspension gelation (S Hjertén: Biochim Biophys Acta 79(2), 393-398 (1964). In an especially advantageous embodiment, the support is a kind of relatively rigid but porous agarose, which is prepared by a method that enhances its flow properties, see e.g. U.S. Pat. No. 6,602,990 (Berg) or SE 0402322-2 (Berg et al.). In an alternative embodiment, the support is prepared from a synthetic polymer or copolymer, such as cross-linked synthetic polymers, e.g. styrene or styrene derivatives, divinylbenzene, acrylamides, acrylate esters, methacrylate esters, vinyl esters, vinyl amides etc. Such synthetic polymers are easily prepared and optionally cross-linked according to standard methods, see e.g. "Styrene based polymer supports developed by suspension polymerization" (R Arshady: Chimica e L'Industria 70(9), 70-75 (1988)). Native or synthetic polymer supports are also available from commercial sources, such as GE Healthcare, Uppsala, Sweden, for example in the form of porous particles. In yet an alternative embodiment, the support is prepared from an inorganic polymer, such as silica. Inorganic porous and non-porous supports are well known in this field and easily prepared according to standard methods.

Suitable particle sizes of the present separation matrix may be in the diameter range of 5-500 µm, such as 10-100 µm, e.g. 20-80 µm. In the case of essentially spherical particles, the average particle size may be in the range of 5-1000 µm, such as 10-500. In a specific embodiment, the average particle size is in the range of 10-200 µm. The skilled person in this field can easily choose the suitable particle size and porosity depending on the process to be used. For example, for a large scale process, for economical reasons, a more porous but rigid support may be preferred to allow processing of large volumes, especially for the capture step. In chromatography, process parameters such as the size and the shape of the column will affect the choice. In an expanded bed process, the matrix commonly contains high density fillers, preferably stainless steel fillers. For other processes other criteria may affect the nature of the matrix.

Thus, a second aspect of the present invention is a separation matrix which comprises the ligands described above coupled to a support. As understood by the skilled person in this field, each support will commonly comprise a plurality of ligands. In a specific embodiment, the support comprise a ligand as described above in combination with a second kind of ligand, wherein the ligand according to the invention is present to at least about 30%, preferably at least about 50%, more preferably at least about 70% and most preferably at least about 90% of the total ligand amount. Such a combined ligand separation matrix may be designed for a specific case, where an element of further interactions improve its separation properties. The second kind of ligand may comprise one or more charged groups, such as a cation exchanger used to elute compounds by charge repulsion; hydrophobic groups; groups capable of hydrogen-bonding; affinity groups or the like.

In a first embodiment, the matrix according to the invention is in the form of particles, such as essentially spherical, elongated or irregularly formed particles. In a specific embodiment, the separation matrix is dried, such as dried particles which upon use are soaked in liquid to retain their original form. In an illustrative embodiment, such a dried separation matrix is comprised of dried agarose particles. However, the matrix according to the invention may alternatively take any other shape conventionally used in separation, such as monoliths; filters or membranes; capillaries; chips; surfaces; etc. Consequently, in a second embodiment, the matrix comprises a membranous structure, such as a single membrane, a pile of membranes or a filter.

A third aspect of the present invention is the use of the separation matrix described above. In a first embodiment, the present invention uses a separation matrix as described above in protein purification. In an advantageous embodiment of the present use, the protein is an antibody; an antibody fragment; or a fusion protein comprising an antibody. In another embodiment, the present invention uses a separation matrix as described above in the separation of any other compound, e.g. one selected from the group consisting of polypeptides; nucleic acids, e.g. DNA, RNA or oligonucleotides thereof; plasmids; virus; prions; cells, such as prokaryotic or eukaryotic cells; lipids; carbohydrates; organic molecules, such as small organic molecules; drug targets; diagnostic marker molecules. The use will be discussed in more detail below. In yet another embodiment, the present invention uses a separation matrix as described above as support in cell culture, i.e. to immobilise cells that grow at surfaces. As the skilled person in this field will realise, in the present application, the term separation is used for purification; isolation; and removal of compounds, but it also encompasses identification of a target compound such as for diagnostic purposes.

A fourth aspect of the present invention is a method of separation, wherein a desired compound such as an antibody is separated from one or more other compounds of a liquid sample by contacting a mobile phase comprising said liquid sample with a separation matrix as described above. In an advantageous embodiment, the present method is carried out using the principles of liquid chromatography, i.e. by passing a mobile phase over a chromatography column comprising the separation matrix according to the invention. In another alternative embodiment, the present method is carried out using a batch-wise chromatography process, wherein the separation matrix is added to a vessel comprising the liquid sample. In a specific embodiment, the separation matrix added in batch-wise mode comprises dried particles, such as dried agarose particles. In another embodiment, the method is carried out using the principles of expanded bed chromatography i.e. by adding the mobile phase to an expanded bed, such as a fluidised bed, of a separation matrix which is in the form of essentially spherical particles comprising high density filler.

In a first embodiment of the present method, undesired compounds are adsorbed to the separation matrix while the desired compound, such as the antibodies, remain in the mobile phase without being adsorbed. As understood by the skilled person in this field, the nature and identity of the adsorbed compounds will depend on the origin of the liquid sample. Examples of compounds adsorbed in the embodiment where desired antibodies are not adsorbed are cells and cell debris; proteins and peptides; nucleic acids, such as DNA and RNA; endotoxins, viruses, residues from the culture media etc. In a specific embodiment, the present separation matrix is provided in a chromatography column and the mobile phase is passed across said column by gravity and/or pumping, the antibodies being recovered in the flow-through of the column. Thus, an advantage of this embodiment is that it does not require any elution of the antibody product from the column. Avoiding a specific elution step is attractive from a process point of view, since fewer steps will result in a more rapid purification protocol and consequently reduce the process costs. In addition antibodies are sensitive to certain conditions that would e.g. impair their folding pattern; or degrade them by attacking their peptide bonds. Thus, even though elution conditions for anion-exchangers in general do not involve any extreme chemicals, the change of salt and/or pH may affect the sensitive antibody, the effect varying from species to species depending on the pI, charge distribution etc. Consequently, another advantage of this embodiment is that it avoids adding an eluent and applying eluting conditions to the desired compounds. To obtain the most suitable conditions for adsorption of compounds, the liquid sample is combined with a suitable buffer or other liquid to provide a mobile phase. The present embodiment is advantageously run under conditions conventional for anion-exchange chromatography, which commonly involves adsorption at a relatively low salt concentration. Thus, in one embodiment of the present method, the conductivity of the mobile phase is in the range of 0-25, such as 10-15 mS/cm. In one embodiment, the pH of the mobile phase is about 5-6. If it is desired to subsequently release the adsorbed compounds, e.g. for re-use of the matrix, elution may be carried out at a higher salt concentration, e.g. by use of an increasing salt gradient. The pH value may also or alternatively be shifted, e.g. be a decreasing pH gradient, to elute adsorbed compounds.

In a second and alternative embodiment of the present method, the desired compounds are adsorbed to the matrix as in conventional liquid chromatography. The matrix may then be reused after selective elution of the product. Elution is easily performed by passing an appropriate buffer over the column. If required, one or more washing steps may be applied before or between any such passage(s). In one embodiment, the operating conditions of this embodiment are as in conventional ion exchange, i.e. adsorption using a mobile phase having low conductivity and elution by using a high conductivity buffer, as discussed above. The skilled person in this field can easily tune the conditions by testing different conditions and analyse the adsorbed compound(s) and flow-through. In a specific embodiment, the desired compounds are antibodies.

Choosing between the first and the second embodiment above, the skilled person in this field can easily adapt the conditions to adsorb a specific compound, advantageously by control of the pH and/or conductivity. For example, in the separation of antibodies, different classes of antibodies have different charges and charge distribution patterns, which together with the purpose of the separation will decide if it is more preferable to adsorb the antibodies or to let them pass the column without being adsorbed.

The antibodies separated according to one embodiment of the present invention may originate from any well known source, such as cells cultured at a surface or from batch-wise or continuous cell culture in fermentation tanks or vessels. Thus, in one embodiment, the liquid is a supernatant obtained from cell fermentation. Examples of compounds that antibodies need to be separated from are then proteins, DNA, viruses, endotoxins, nutrients, components of a cell culture medium, such as antifoam agents and antibiotics, and product-related impurities, such as misfolded species and aggregates. The step of contact between the mobile phase and the present separation matrix, i.e. the adsorption step, may be preceded by a step of mechanical filtration, centrifugation and/or chromatography. For example, if the liquid sample is a fermentation broth, it is advantageous to mechanically remove cell debris, whole cells and other relatively large components before the step using the present matrix.

In one embodiment, the present method constitutes the capture step of a purification protocol. In a specific embodiment, the liquid sample is a crude feed which is filtrated before contact with the chromatography matrix according to the invention. Consequently, this embodiment would still constitute a capture step, even though the liquid sample has been prepurified by mechanical means. As is well known, the host cells that produce antibodies will also comprise a number of other proteins commonly known as host cell proteins (HCP). Such HCPs include enzymes, such as proteases, and other proteins produced by the host cells. Thus, in one embodiment, substantially all host cell proteins of the liquid sample are removed by the present method, such as by adsorption to the separation matrix.

In alternative embodiments, the present method is used as a second, third or even fourth chromatography step in a cleaning protocol, such as an intermediate purification or polishing step. Thus, in one embodiment, the mobile phase applied to the present separation matrix comprises an antibody-containing eluate from a separation matrix. In one embodiment, the liquid sample is an eluate from a preceding affinity chromatography matrix. In an advantageous embodiment, the separation matrix from which the eluate is obtained comprises one or more Fc-binding protein ligands, such as Protein A ligands. The term protein A ligands includes in this context native as well as recombinant protein A, or functional fragments thereof. In this context, the term "functional" fragment means a fragment that has retained the original binding properties of the protein. Such affinity matrices are commercially available, such as MabSelect™ from GE Healthcare. Consequently, in this embodiment, the removed, preferably adsorbed compound may be one or more selected from the group that consists of released Protein A; complexes formed between Protein A and antibodies, such as Protein A-MAb complexes, which complexes may comprise a number of antibodies per Protein A molecule, such as 2-4 antibodies complexed with one Protein A molecule; and aggregates of released Protein A or antibodies. As the skilled person in this field will understand, depending on the specific conditions used in the preceding step, such as affinity chromatography, the eluate may need conditioning by suitable additions or adjustment. Thus, the eluate is combined with a suitable buffer or liquid to provide a mobile phase.

The present method is useful to separate any monoclonal or polyclonal antibody, such as antibodies originating from mammalian hosts, e.g. mice, rodents, primates and humans, or antibodies originating from hybridomas. In one embodiment, the separated antibodies are human or humanised antibodies. The antibodies may be of any class, i.e. selected from the group that consists of IgA, IgD, IgE, IgG, and IgM. In one embodiment, the antibodies are antibodies capable of binding to Protein A, or Fc-containing antibody fragments or fusion proteins. In a specific embodiment, the antibodies are immunoglobulin G (IgG), such as IgG1. In one embodiment, the present method is used to purify antibodies having a pI in the range of 6-9, such as in the range of 7-8. In a specific embodiment, the pI of the purified antibodies is about 9. In the present context, it is to be understood that the term "antibodies" also includes antibody fragments and any fusion protein that comprises an antibody or an antibody fragment. Thus, the present invention also encompasses the separation of fragments of any one of the above mentioned antibodies as well as fusion proteins comprising such antibodies. In one embodiment, the antibodies are monoclonal antibodies. In a specific embodiment, the antibodies are humanised antibodies.

As appears from the above, in the present method, a substantially pure fraction of non-adsorbed antibodies is recovered. In this context, the term "substantially pure" is understood to mean that substantially all the non-antibody compounds have been removed. Most advantageously, at least about 80%, such as at least about 95%, i.e. in the interval of 95-100%, such as at least about 98%, i.e. in the interval of 98-100% and preferably at least about 99%, i.e. in the interval of 99-100%, of the total amount of contaminants is removed on the present separation matrix. However, as the skilled person in this field will appreciate, the purity obtained will depend on the concentration of antibody in the liquid sample applied to the separation matrix as well as other conditions used. Thus, in one embodiment, the antibodies separated according to the present method are antibodies of therapeutic grade. Thus, the antibodies purified according to the invention are useful in research and also for the preparation of antibody pharmaceuticals, such as MAb drugs. An alternative use of the purified antibodies is for diagnostic use. Further, the purified antibodies are also useful in food products such as food additives for humans. For example, bovine antibodies purified according to the present invention are useful in food products.

In a specific embodiment of the present method, the present separation matrix is provided as a disposable chromatography column or a disposable filter. An advantage of using disposable products in a method for purification of therapeutic compounds such as antibodies is that it enables avoiding cross-contamination between two different processes. Thus, in one embodiment, the present separation matrix is provided as a sterile chromatography column or filter. In one embodiment, the present method is carried out as a batch-wise process, wherein a disposable separation matrix is added to a vessel comprising the liquid from which the antibodies are to be recovered. A suitable time is allowed for target compounds to adsorb to the matrix, after which the liquid phase comprising the antibodies is removed from the vessel. The used matrix may then be disposed of, without releasing the adsorbed compounds, which again may be advantageous from a safety point of view since compounds such as endotoxins and/or certain host cell proteins need not be handled any further. In an alternative embodiment, the present matrix is provided as a disposable product in a chromatography column which is used in a mode wherein the antibodies are adsorbed. In an advantageous embodiment, the column and matrix have been sterilized, allowing the user to purify antibody product under aseptic or even sterile conditions.

In a second aspect, the present invention relates to a kit for the purification of antibodies from one or more other components in a liquid, which kit comprises in separate compartments a chromatography column packed with a separation matrix as described above; one or more buffers; and written instructions. The separation matrix may be as described above. Said instructions advantageously describe a method as defined above in detail.

DETAILED DESCRIPTION OF THE DRAWINGS

FIG. 1 shows the prototype ligand N-benzyl-N-methyl ethanolamine as immobilised via the nitrogen atom to a support in the form of a bead. The coupled ligand is shown to the left with the linker schematically drawn; and to the right with an illustrative hydrophilic linker. In the experimental part, the prototype ligand was coupled to the 6% agarose matrix Sepharose™ 6 FF (GE Healthcare, Uppsala, Sweden).

Figure 2:
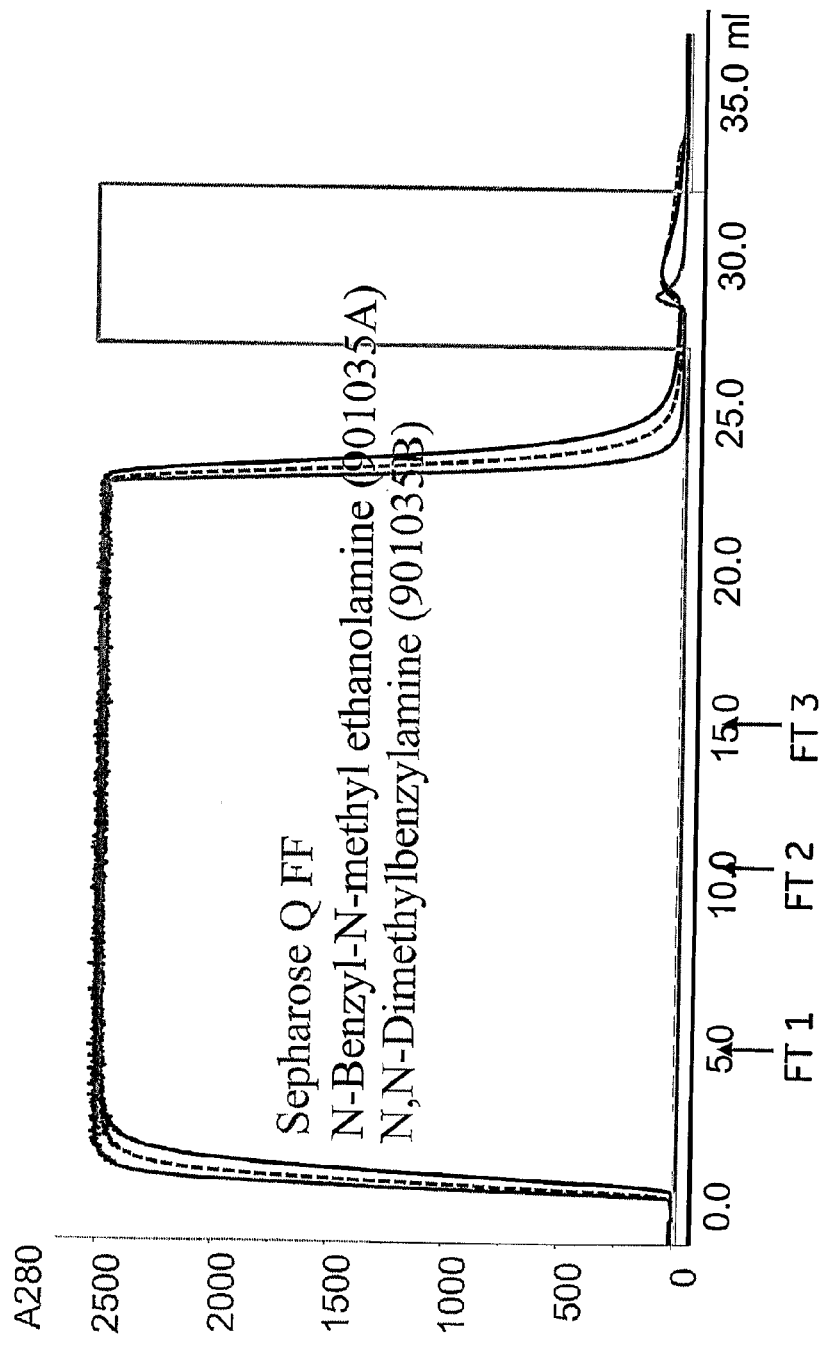
FIG. 2 shows a chromatogram of separation of monoclonal antibody on a separation matrix comprising N-benzyl-N-methyl ethanolamine ligands immobilised onto Sepharose™ 6 FF; and for reference, the strong anion-exchanger Q Sepharose™ FF, as described below.

FIG. 2 shows a chromatogram of sample containing 50 mg Mab1 applied to separation matrices comprising ligands of N-benzyl-N-methyl ethanolamine immobilised on Sepharose™ 6 FF (901035A); N,N-dimethylbenzylamine immobilised on Sepharose 6FF; and Q Sepharose™ FF in 25 mM Bis-Tris, 100 mM NaCl (~12 mS/cm), pH 6.5. Elution was performed with 25 mM Bis-Tris, 0.5 M NaCl, pH 6.5.

FIG. 3a) and b) show the results of chromatography carried out on prototypes with mAb1-rProtein A. A-buffer was 25 mM Bis-Tris, 50 mM NaCl, pH 6.0. The conductivity was approximately 7 mS/cm. B-buffer, 0.5 M Na-Acetate, pH 4.0, was used for elution. Flow rate was 0.5 mL/min (150 cm/h). Sample was 10 mg mAb1, 0.10 mg rPrA at a concentration of 4 mg/ml mAb1 and 1% rProtein A (w/w). 3a) ref. Q Sepharose™ FF; and b) N-benzyl-N-methylethanolamine, 146 μmol/mL (901035A).

Figure 3:
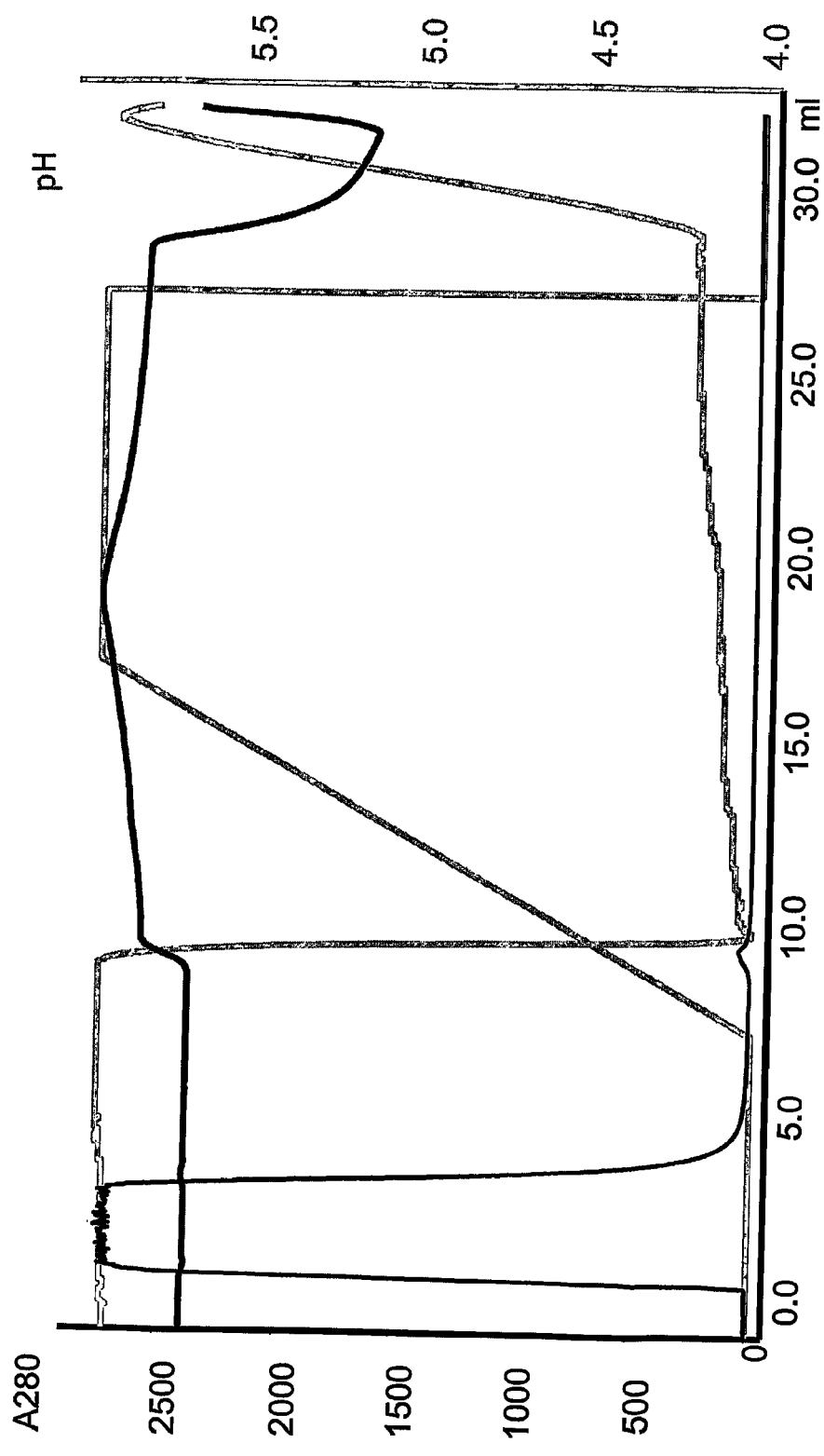
FIG. 3a) and b) show the results of chromatography carried out on ligand prototypes with a mixture of mAb1-rProtein A.
Figure 3:
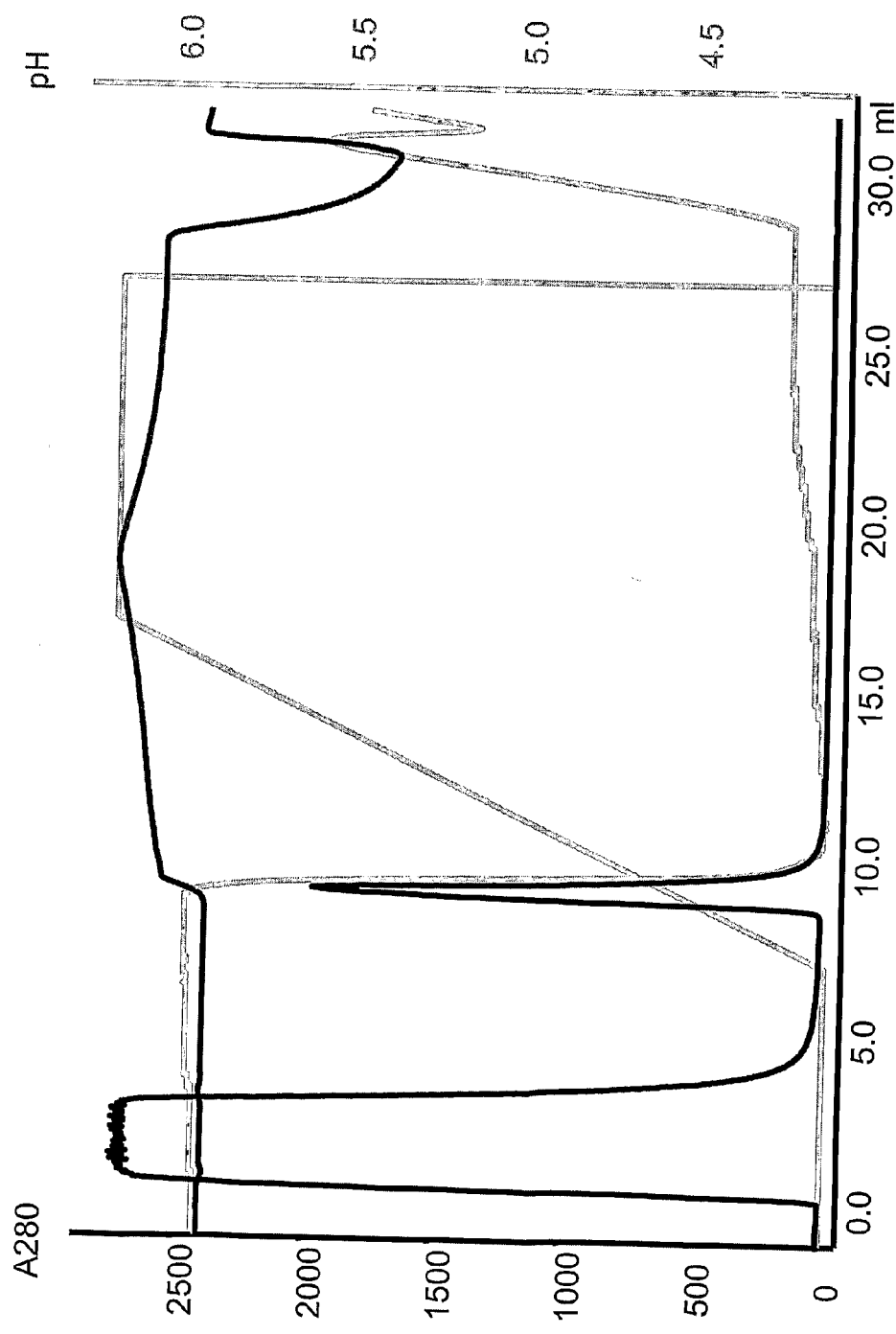
Figure 4A:
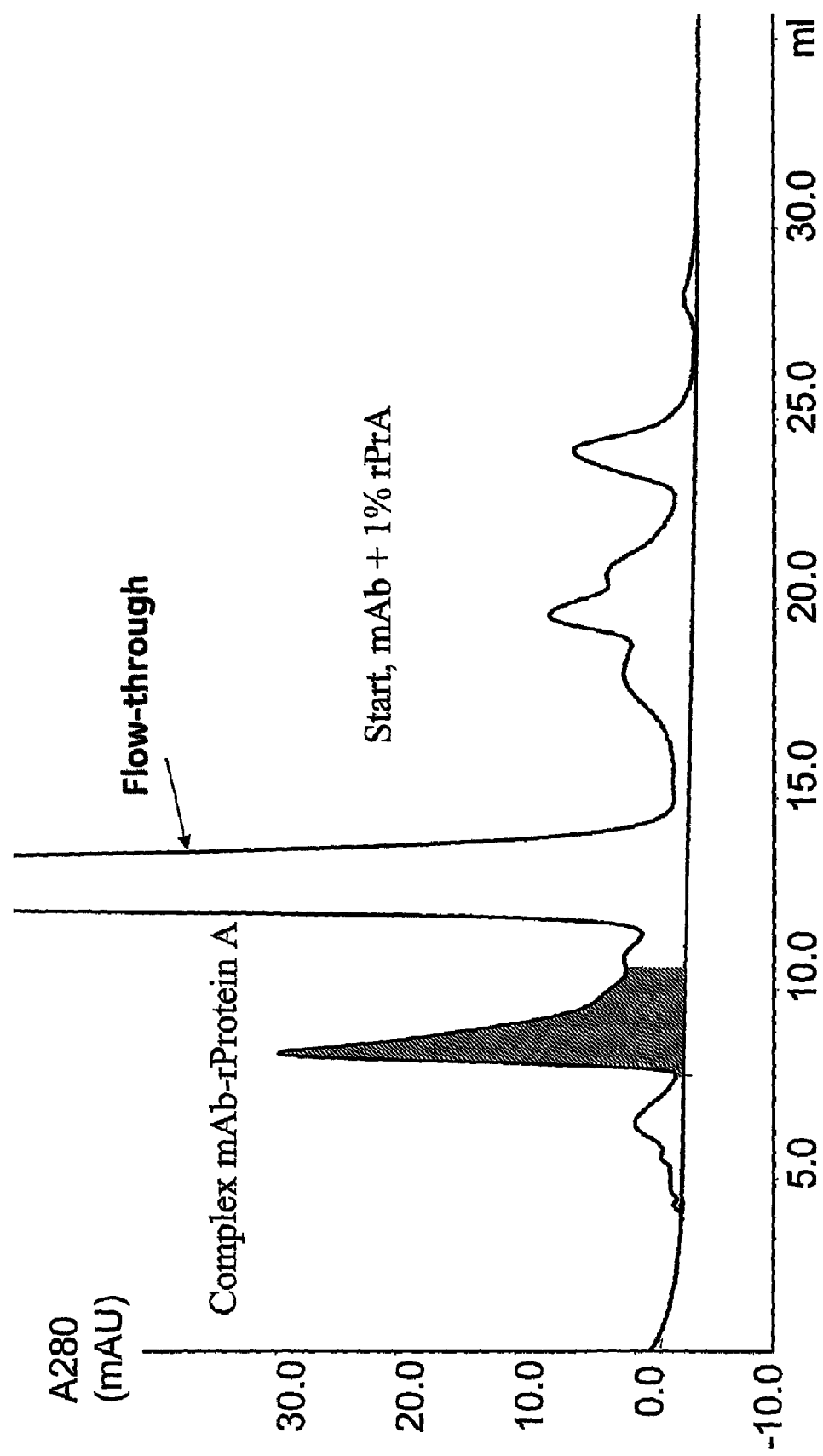
FIG. 4a)-c) show the results of analytical size exclusion chromatography (SEC) on sample with MAb 1, 1% rPrA and pooled flow-through and eluate fractions from the chromatographic runs in FIG. 3.

FIG. 4a)-c) show the results of analytical size exclusion chromatography (SEC) on sample with MAb 1, 1% rPrA and pooled flow-through and eluate fractions from the chromatographic runs in FIG. 3. The blue curve is flow-through (FT) fractions and the red is eluate. More specifically, FIG. 4a) shows a sample of 4 mg/mL mAb1, 0.04 mg/mL rPrA giving 1% (w/w); 4b) shows FT and eluate from FIG. 3a) Q Sepharose™ FF; and 4c) shows FT and eluate from FIG. 3b) N-benzyl-N-methylethanolamine, 146 μmol/mL (901035A).

EXPERIMENTAL PART

The present examples are provided for illustrative purposes only, and should not be interpreted in any way as limiting the scope of the invention as defined by the appended claims.

EXAMPLE 1

Preparation of Separation Matrix According to the Invention

Preparation of BMEA Sepharose Fast Flow

One embodiment of the method of preparing a separation matrix according to the invention is shown below, starting from a crosslinked agarose gel (Sepharose™ 6 Fast Flow, GE Healthcare, Uppsala, Sweden).

A. Introduction of Allyl Group on the Matrix

Sepharose 6 Fast Flow was activated with allyl glycidyl ether as follows: 100 ml of Sepharose 6 Fast Flow was suction dried, mixed with 0.3 g of $NaBH_4$, 12 g of $Na_2SO_4$ and 35 ml of 50% aqueous solution of NaOH. The mixture was stirred for 1 hour at 50° C. After addition of 100 ml of allyl glycidyl ether the suspension was left at 50° C. under vigorous stirring for an additional 16 hours. After filtration of the mixture, the gel was washed successively, with 500 ml distilled water, 500 ml ethanol, 200 ml distilled water 200 ml 0.2 M acetic acid and, 500 ml distilled water.

Titration gave a degree of substitution of 0.22 mmol of allyl/ml of gel.

B. Activation of Allyl Sepharose 6 Fast Flow via Bromination

Bromine was added to a stirred suspension of 50 ml of allyl activated Sepharose 6 Fast Flow (0.22 mmol allyl groups/ml drained gel), 1 g of sodium acetate and 15 ml of distilled water, until a persistent yellow colour was obtained. Sodium formate was then added until the suspension was filly decolourised. The reaction mixture was filtered and the gel washed with 500 ml of distilled water. The activated gel was then directly transferred to a reaction vessel and further reacted with N-benzyl-N-methylethanolamine.

C. Introduction of BMEA (N-benzyl-N-methylethanolamine) Groups on the Activated Matrix The amine groups were introduced on the matrix directly via the nitrogen atom of the amine groups. In a typical procedure, the coupling to the matrix was realised via bromination of the allyl group and nucleophilic substitution under basic conditions. 25 ml of bromine activated gel (0.22 mmol allyl groups/ml drained gel) was transferred to a reaction vial containing a solution of N-benzyl-N-methylethanolamine (16.0 ml). 5 ml of water was added and the pH of the reaction solution was adjusted to 12.0 with sodium hydroxide solution. The reaction was left for 16 hours under stirring at 50° C. After filtration of the reaction mixture the gel was successively washed with 3×10 ml of distilled water, 3×10 ml aqueous 0.5 HCl and finally 3×10 ml of distilled water. BMEA Sepharose Fast Flow gel was obtained with a degree of substitution of 0.15 mmol amines/ml of gel.

EXAMPLE 2

Purification of Antibodies in the Flow-through

EXAMPLE 2A)

Disposition

Under non-binding conditions, sample containing approximately 50 mg mAb1 were loaded onto prototype 901035 A (N-benzyl-N-methyl ethanolamine) at approximately 5 and 12 mS/cm. Flow-through fractions (FT) were collected at 5, 10 and 15 column volumes (CV). Fractions from the elution peak were pooled. FT fractions were analysed for HCP and Protein A content.

To confirm that the chromatographic performance was not unique for one particular mAb, the chromatographic runs were repeated using a sample containing mAb2 at pH 6.0 and approximately 12 mS/cm. The performance of the prototype was first evaluated with analytical SEC. Selected fractions were analysed for HCP and Protein A content. After screening the fractions with SEC selected fractions were sent for HCP and Protein A analysis.

To test the rProtein A clearance of the prototype, MAb1 was spiked with 1% (w/w) recombinant Protein A (rPrA). The prototype was injected with a sample volume corresponding to 10 mg MAb1, 1% rProtein A at pH 6.0 and a conductivity of approximately 7 mS/cm. Flow-through and eluate fractions were pooled separately and analysed with SEC.

Materials/Investigated units
Columns and gels were obtained from GE Healthcare, Uppsala, Sweden

| | | |
|---|---|---|
| HiPrep ™ 26/10 Desalting | cat. no. 17-5087-01 | CV = 53.09 mL |
| Tricorn ™ 5/50 | cat. no. 18-1163-09 | CV = 1 mL |
| HR 5/5 ™ | cat. no. 18-0338-01 | CV = 1 mL |
| Superdex ™ 200 10/300 GL, | cat. no. 17-5175-01 | CV = 23.56 mL |

Instruments

| | |
|---|---|
| Chromatography systems: | ÄKTAExplorer ™ 10 |
| Spectrophotometer | Spectra MAX plus |

Chemicals

All chemicals used were of analytical grade. Water was MilliQ-filtered.

Chromatography Media

Q Sepharose™ Fast Flow (FF) (GE Healthcare, Uppsala, Sweden). The ligands of the separation matrices are prototypes as described in Table 1 below.

TABLE 1

| | Ligand | |
|---|---|---|
| Prototype ref. | Ligand | Cl⁻capacity ($\mu$mol/mL) |
| 901035A | N-benzyl-N-methyl ethanolamine | 146 |

Samples

Two different humanised IgG antibodies, subclass 1, denoted MAb 1 and MAb 2, with an extinction coefficient of 1.46 and 1.50 respectively, were used. Both antibodies were expressed in a CHO cultures and subsequently purified using conventional Protein A affinity chromatography prior to the present experiments.

Buffer exchange was made on a HiPrep™ Desalting column (GE Healthcare, Uppsala, Sweden), equilibrated with the buffer of interest, by injecting an appropriate volume (5-15 mL) with a Superloop™ (GE Healthcare, Uppsala, Sweden). The flow rate was 5 mL/min and fractions of 5 mL were collected. Fractions containing the eluted peak were pooled and the absorbance at 280 nm determined in duplicates, in order to calculate the concentration according to equation 1:

$$A_{280} = \epsilon \cdot C \cdot l \qquad \text{(Eqn 1)}$$

wherein $A_{280}$ is the absorbance at 280 nm.

$\epsilon(mL*mg^{-1}*cm^{-1})$ is the extinction coefficient for a particular protein.

C(mg/mL) is the concentration of the protein.

l (cm) is the path length.

Size exclusion chromatography (SEC) was performed on a Superdex™ 200 10/300 column (GE Healthcare, Uppsala, Sweden) at a flow rate of 0.5 mL/min. The buffer was PBS (phosphate-buffered saline); 10 mM phosphate, 0.137 M NaCl, 2.7 mM KCl, pH 7.4 prepared from tablets (Sigma, P-4417).

Method

| | | |
|---|---|---|
| Equilibration | 2/0.1 CV; | 2 CV first time use; 0.1 CV between runs |
| Sample injection | 50 μl | |
| Isocratic Elution | 1.5 CV | |

Chromatography on Prototypes with mAb

A-buffer was 25 mM Bis-Tris, pH 6.0 or 6.5. Depending on the desired conductivity, approximately 5 or 12 mS/cm, 35 or 100 mM NaCl was included. The elution buffer (B-buffer) was 25 mM Bis-Tris, 0.5 M NaCl, pH 6.5. The flow rate was 0.5 mL/min (150 cm/h).

| Method: | Equilibration | 5 CV | A-buffer |
|---|---|---|---|
| | Sample injection | 5-25 mL | sample cont. 20 or 50 mg mAb |
| | Wash | 5 CV | A-buffer |
| | Gradient Elution | 10 CV | 0-100% B-buffer |
| | Elution | 10 CV | 100% B-buffer |
| | Regeneration | 5 CV | A-buffer |

Chromatography on Prototypes with MAb-rProtein A

A-buffer was 25 mM Bis-Tris, pH 6.0. The conductivity was approximately 7 mS/cm by addition of 50 mM NaCl, B-buffer was 0.5 M Na-acetate, pH 4.0. Flow rate was 0.5 mL/min (150 cm/h). Sample concentration was 4 mg/mL MAb 1-0.04 mg/mL rPrA giving 1% (w/w).

| Method: | Equilibration | 5 CV | A-buffer |
|---|---|---|---|
| | Sample injection | 2.5 mL | 10 mg MAb, 1% rPrA |
| | Wash | 5 CV | A-buffer |
| | Gradient Elution | 10 CV | 0-100% B-buffer |
| | Elution | 10 CV | 100% B-buffer |
| | Regeneration | 5 CV | A-buffer |

CIP (Cleaning in Place)

After each chromatographic run, the prototype and the reference matrix Q Sepharose™ FF were subject to the following CIP procedure;

| 30% isopropanol | 5 CV (Column Volumes) |
|---|---|
| $H_2O$ | 5 CV |
| 1.0 M NaOH | 4 CV (incl. 15 min. pause) |
| $H_2O$ | 5 CV |
| A-buffer | 5 CV |
| $H_2O$ | 5 CV |
| 20% EtOH | 5 CV |

Protein A Analysis

Selected fractions were mixed with SPA sample diluent in proportions of 800 μl SPA sample diluent +200 μl sample. After mixing, the fractions were heated on a heating block at 99° C. for 10 minutes, then mixed again. The samples were then analysed for recombinant Protein A.

Host Cell Proteins (HCP) Analysis

The samples (min. 600 μl) were analysed for HCP content. The lower detection limit is 10 ng/mL.

EXAMPLE 2B)

MAb1-containing Sample Purified on Prototype Ligands N-benzyl-N-methylethanolamine (901035A)

Sample containing 50 mg MAb1 was applied to N-benzyl-N-methyl ethanolamine immobilised on Sepharose™ 6 FF (901035A) prepared as described in Example 1 above and the reference matrix Q Sepharose™ FF in 25 mM Bis-Tris, 100 mM NaCl (~12 mS/cm), pH 6.5. Elution was carried out with 25 mM Bis-Tris, 0.5 M NaCl, pH 6.5.

The chromatograms of example 2 are shown in FIG. 2, which shows the prototype N-benzyl-N-methyl ethanolamine Sepharose™ 6 FF (901035A) compared to Q Sepharose™ FF. Flow-through (FT) fractions selected for analysis are indicated with arrows. The results for HCP and Protein A clearance shown in tables 2 and 3 below reveal that the prototype is superior to Q Sepharose™ FF in that respect.

TABLE 2

Results from HCP analysis

| Column | pH | Start (ng/mL) | FT1 (ng/mL) | FT2 (ng/mL) | FT3 (ng/mL) |
|---|---|---|---|---|---|
| Q Sepharose ™ FF (ref) | 6.5 | 890 | 160 | 200 | 180 |
| N-benzyl-N-methylethanolamine, 146 μmol/mL (901035A) | 6.5 | 890 | 10 | 20 | 35 |

TABLE 3

Results from PrA analysis

| Column | pH | Start (ng/mL) | FT1 (ng/mL) | FT2 (ng/mL) | FT3 (ng/mL) |
|---|---|---|---|---|---|
| Q Sepharose ™ FF (ref) | 6.5 | 0.40 | 0.69 | 0.46 | 0.31 |
| N-benzyl-N-methylethanolamine, 146 μmol/mL (901035A) | 6.5 | 0.40 | 0 | 0 | 0 |

EXAMPLE 3

Purification of MAb1 in the Flow Through from a Sample Comprising MAb1 and Recombinant Protein A (rPrA) on Prototype Ligand N-benzyl-N-methylethanolamine In this example, chromatography on prototypes with a sample containing mAb1-rProtein A was performed. A-buffer was 25 mM Bis-Tris, 50 mM NaCl, pH 6.0. The conductivity was approximately 7 mS/cm. B-buffer was 0.5 M Na-Acetate, pH 4.0. The flow rate was 0.5 mL/min (150 cm/h). Sample was 10 mg mAb1, 0.10 mg rPrA at a concentration of 4 mg/ml mAb1 and 1% rProtein A (w/w). The results are shown in FIG. 3.

Figure 4C:
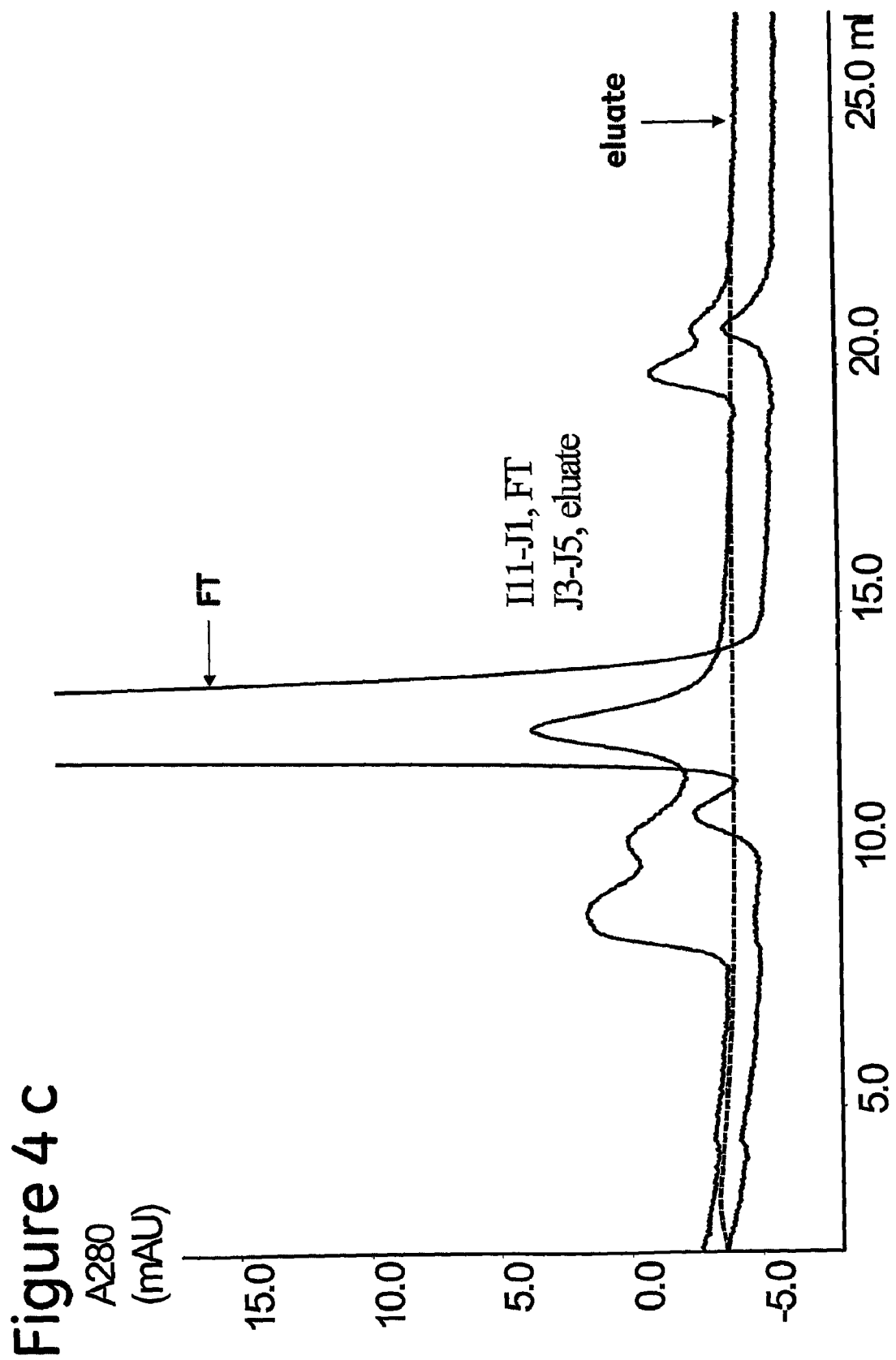

Finally, analytical SEC on sample with mAb1, 1% rPrA and pooled flow-through and eluate fractions from the chromatographic runs in FIG. 4 were performed. The results are shown in FIG. 4. In FIG. 4a, the shaded peak is the complex of MAb1-Protein A. The blue curve is the flow-through (FT) fractions and the red is the eluate.

EXAMPLE 4

Adsorption Mode

EXAMPLE 4A

Disposition

To test the selectivity of BMEA Sepharose Fast Flow (BMEA; N-benzyl-N-methylethanolamine) in adsorptive mode the retention time of human IgG and eight different proteins was tested. The results were compared to a commercially available anion exchanger Q Sepharose Fast Flow. The principle of the test method was that proteins were injected into an HR5/5 column (containing the BMEA ligands immobilised on Sepharose™ Fast Flow) equilibrated with the A-buffer (containing piperazine as buffer component). A salt gradient was used for elution of the proteins (see method below).

Materials/Investigated Units

Columns and Q Sepharose Fast Flow were obtained from GE Healthcare, Uppsala, Sweden.

HR 5/5™: cat.no. 18-0338-01 Column Volume (CV=1 mL)

Instrument

Chromatography systems: ÄKTAExplore™ 10

Chemicals and Samples

The proteins, ovalbumin, β-lactoglobulin, bovine serum albumin, α-lactalbumin, myoglobin, lactoferrin, ribonuclease A and cytochrome C were purchased from Sigma and human IgG (Gammanorm) was purchased from Octapharma. The proteins were dissolved in the A-buffers at a concentration of 1-10 mg/ml. Q Sepharose Fast Flow was obtained from GE Healthcare, Uppsala Sweden. All chemicals used were of analytical grade and the water used was MilliQ-filtered.

Chromatography

The columns were equilibrated with the A-buffer at a flow rate of 0.6 ml/min before 100 μl of the sample solution were applied. Only one protein at a time was analysed. The proteins were eluted by a linear gradient from buffer A to buffer B with a gradient volume of 21 column volumes (see method below). The buffer A was 25 mM Piperazine, pH 10.0 and buffer B was 25 mM Piperazine, 1.0 M NaCl, pH 10.0. The absorbance at 280 nm was detected during all runs.

| Method: | | |
|---|---|---|
| | Equilibration: | 5 CV of A-buffer |
| | Sample injection: | 100 μl (ca 0.2 mg protein) |
| | Gradient: | 21 CV 100% B-buffer |
| | Equilibration after gradient: | 5 CV of A-buffer |

Results

To document if the BMEA ligand interact selectively with immunoglobulines, human IgG was applied to a 1 ml column (HR 5/5) packed with the new medium. In addition, the proteins ovalbumin, β-lactoglobulin, bovine serum albumin, α-lactalbumin, myoglobin, lactoferrin, ribonuclease A and cytochrome C were also applied. The results were compared with the retention times of the proteins observed for Q Sepharose Fast Flow. Q Sepharose Fast Flow is a strong anion-exchanger and is used as reference anion exchanger since it has the same support matrix (support material, bead size, pore sizes, pore volume, packing procedure etc) and has essentially the same substitution degree (measured as ion exchange capacity). As appears from Table 1 BMEA Sepharose Fast Flow retarded all the investigated proteins more strongly compared with Q Sepharose Fast Flow. Furthermore, IgG was the protein that gave the longest retention time with BMEA Sepharose Fast Flow (Table 1).This reflects a much stronger binding to the BMEA medium than to Q Sepharose Fast Flow. Compared to Q Sepharose Fast Flow the retention time of IgG increased 27.3 min when BMEA Sepharose Fast Flow was used (Table 1). These results clearly indicate that BMEA Sepharose Fast Flow can be used to capture and elute IgG in a selective way.

TABLE 1

Retention time ($t_r$) of different proteins on Q Sepharose Fast Flow and BMEA Sepharose Fast Flow.

| Protein | Molecular weight | pI | $t_r$ on Q Sepharose Fast Flow (min) | $t_r$ on BMEA Sepharose Fast Flow (min) | $\Delta t_r$ ($t_r$ BMEA – $t_r$ Q) |
|---|---|---|---|---|---|
| Cytochrome C | 12400 | 9.6 | 15.3 | 16.8 | 1.5 |
| Ribonuclease A | 13700 | 9.4 | 15.8 | 22.6 | 6.8 |
| Lactoferrin | 75000 | 7.9 | 15.1 | 19.4 | 4.3 |
| Myoglobin | 17600 | 7.2 | 16.1 | 20.5 | 4.4 |
| Human IgG | 160000 | | 16.5 | 43.8 | 27.3 |
| α-Lactalbumin | 14400 | 5.2 | 24.6 | 40.3 | 15.7 |
| Bovine serum albumin | 69000 | 5.1 | 25.3 | 32.6 | 7.3 |
| β-Lactoglobulin | 35000 | 5.1 | 25.1 | 37.1 | 12.0 |
| β-Lactoglobulin | 35000 | 5.1 | 30.0[x] | 37.1 | 7.1 |
| Ovalbumin | 43500 | 4.7 | 21.8 | 30.8 | 9.0 | na = not analyzed,
[x]Two peaks were observed

The invention claimed is:

1. A separation matrix comprising N-benzyl-N-methyl ethanol amine ligands coupled to a support, wherein said support is linked to nitrogen atom of the ligand through a linker.

* * * * *